United States Patent
Scheer

(10) Patent No.: US 7,483,804 B2
(45) Date of Patent: Jan. 27, 2009

(54) METHOD OF REAL TIME DYNAMIC CD CONTROL

(75) Inventor: Steven Scheer, Austin, TX (US)

(73) Assignee: Tokyo Electron Limited, Tokyo (JP)

( * ) Notice: Subject to any disclaimer, the term of this patent is extended or adjusted under 35 U.S.C. 154(b) by 169 days.

(21) Appl. No.: 11/537,085

(22) Filed: Sep. 29, 2006

(65) Prior Publication Data

US 2008/0079934 A1 Apr. 3, 2008

(51) Int. Cl.
*G01N 21/00* (2006.01)
*G03B 27/72* (2006.01)
*G03C 5/00* (2006.01)
*G06F 15/00* (2006.01)

(52) U.S. Cl. .......................... 702/127; 355/69; 430/30; 356/237.4

(58) Field of Classification Search .................. 702/33, 702/127; 356/237.3, 237.4, 635, 636; 432/1, 432/241, 247, 253; 355/53, 69
See application file for complete search history.

(56) References Cited

U.S. PATENT DOCUMENTS

| 6,806,008 B2 * | 10/2004 | Schedel et al. ................. 430/30 |
| 7,101,816 B2 | 9/2006 | Kaushal et al. |
| 2006/0192936 A1 * | 8/2006 | Schenau et al. ............... 355/69 |
| 2006/0222975 A1 * | 10/2006 | Ke et al. ....................... 430/30 |

* cited by examiner

*Primary Examiner*—Bryan Bui
(74) *Attorney, Agent, or Firm*—Wood, Herron & Evans, LLP

(57) ABSTRACT

A method of real time dynamic CD control in a system for patterning resist coated wafers. The method includes lithographically patterning the resist coated wafers using predetermined exposure dose and focus settings. The method further includes obtaining CD metrology data from test areas on the patterned wafers, where different groups of test areas are selected for two or more of the patterned wafers. A CD metrology data map is constructed using the CD metrology data, adjusted exposure dose and/or focus settings are established using the CD metrology data, and additional wafers are then patterned.

21 Claims, 12 Drawing Sheets

METHOD OF REAL TIME DYNAMIC CD CONTROL

CROSS-REFERENCE TO RELATED APPLICATIONS

This application is related to co-pending U.S. patent application Ser. No. 11/536,991, entitled "METHOD OF REAL TIME DYNAMIC CD CONTROL," filed on even date herewith, the entire content of which is hereby incorporated by reference. This application is also related to co-pending U.S. patent application Ser. No. 11/536,978, entitled "METHOD FOR IN-LINE MONITORING AND COTROLLING IN HEAT-TREANING OF RESIST COATED WAFERS," filed on even date herewith, the entire content of which is hereby incorporated by reference.

FIELD OF THE INVENTION

The invention relates to a method for processing wafers, and more particularly, to a method of real time dynamic critical dimension (CD) control and optimization for lithographically patterned wafers.

BACKGROUND OF THE INVENTION

In a photolithography process for manufacturing semiconductor devices and liquid crystal displays (LCD's), resist is coated on a substrate, and the resultant photoresist coating film is exposed to light and developed. The series of processing stages are carried out in a coating/developing processing system having discrete heating sections, such as a prebaking unit and a postbaking unit. Each heating section incorporates a hotplate with a built-in heater of a resistance heating type.

Feature sizes of semiconductor device circuits have been reduced to less than 0.1 microns. Typically, the pattern wiring that interconnects individual device circuits is formed with sub-micron line widths. To provide reproducible and accurate feature sizes and line widths, it has been strongly desired to control more accurately light exposure parameters and the heat treatment temperature of the photoresist film. The substrates or wafers (i.e., objects to be treated) are usually treated or processed under the same recipe (i.e., individual treatment program) in units (i.e., lots) each consisting of, for example, twenty-five wafers. Individual recipes define heat treatment conditions under which prebaking and postbaking are performed. Wafers belonging to the same lot are heated under the same conditions.

Heat-treating a photoresist plays an important role in the photoresist processing and may have many purposes, from removing a solvent from the photoresist to catalyzing chemical amplification in the photoresist. In addition to the intended results, heat-treating may cause numerous problems. For example, the light sensitive component of the photoresist may decompose at temperatures typically used to remove the solvent, which is an extremely serious concern for a chemically amplified resist (CAR) since the remaining solvent content has a strong impact on the diffusion and amplification rates. Also, heat-treating can affect the dissolution properties of the resist and thus have direct influence on the developed resist profile. CAR's are particularly sensitive to temperature variations during heat treatment and temperature variations can result in variations in critical dimensions (CDs) across a wafer surface.

Therefore, real time metrology data collection of physical properties of processed resist coated wafers is required in order to optimize light exposure parameters and the temperature profile across the wafers in the heat-treating process. New methods are needed that provide the high metrology data density required for controlling and optimizing the light exposure and heat-treating process, while allowing for high wafer throughput.

SUMMARY OF THE INVENTION

Embodiments of the invention provide a method of real time dynamic critical dimension (CD) control and optimization for a process of lithographically patterning resist coated wafers. The method provides the high metrology data density required for controlling and optimizing the patterning process, while allowing for high wafer throughput.

According to one embodiment of the invention, the method includes lithographically patterning resist coated wafers using predetermined exposure dose and focus settings. The method further includes obtaining CD metrology data from test areas on the patterned wafers, wherein different groups of test areas are selected for two or more of the patterned wafers. A CD metrology data map is constructed from the CD metrology data and adjusted exposure and focus settings are established using the CD metrology data map. Subsequently, additional wafers may be patterned.

BRIEF DESCRIPTION OF THE DRAWINGS

A more complete appreciation of the invention and many of the attendant advantages thereof will become readily apparent with reference to the following detailed description, particularly when considered in conjunction with the accompanying drawings, in which.

DETAILED DESCRIPTION OF SEVERAL EMBODIMENTS

Embodiments of the invention provide a method for real time dynamic CD control and optimization associated with lithographically patterning resist coated wafers on a hotplate. The method provides high density CD metrology data collection for CD control and optimization while allowing high wafer throughput. According to one embodiment of the invention, the method includes constructing a CD metrology data map from CD metrology data obtained from test areas on the patterned wafers, where different groups of test areas are selected for two or more of the patterned wafers. Adjusted exposure and focus settings are established using the CD metrology data map to pattern additional resist coated wafers.

The terms "wafer" and "substrate" are used interchangeably herein to refer to a thin slice of material, such as a silicon crystal or glass material, upon which microcircuits are constructed, for example by diffusion, deposition, and etching of various materials.

Figure 1:
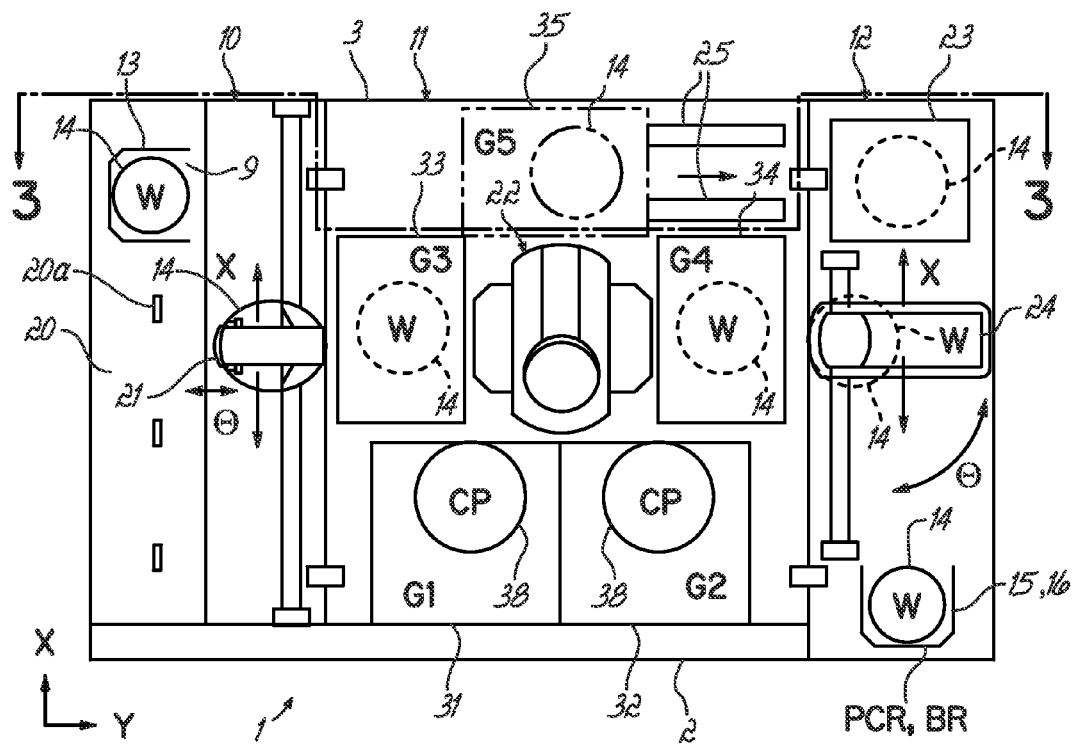
FIG. 1 is a top view of a schematic diagram of a coating/developing system for use in accordance with embodiments of the invention.
Figure 2:
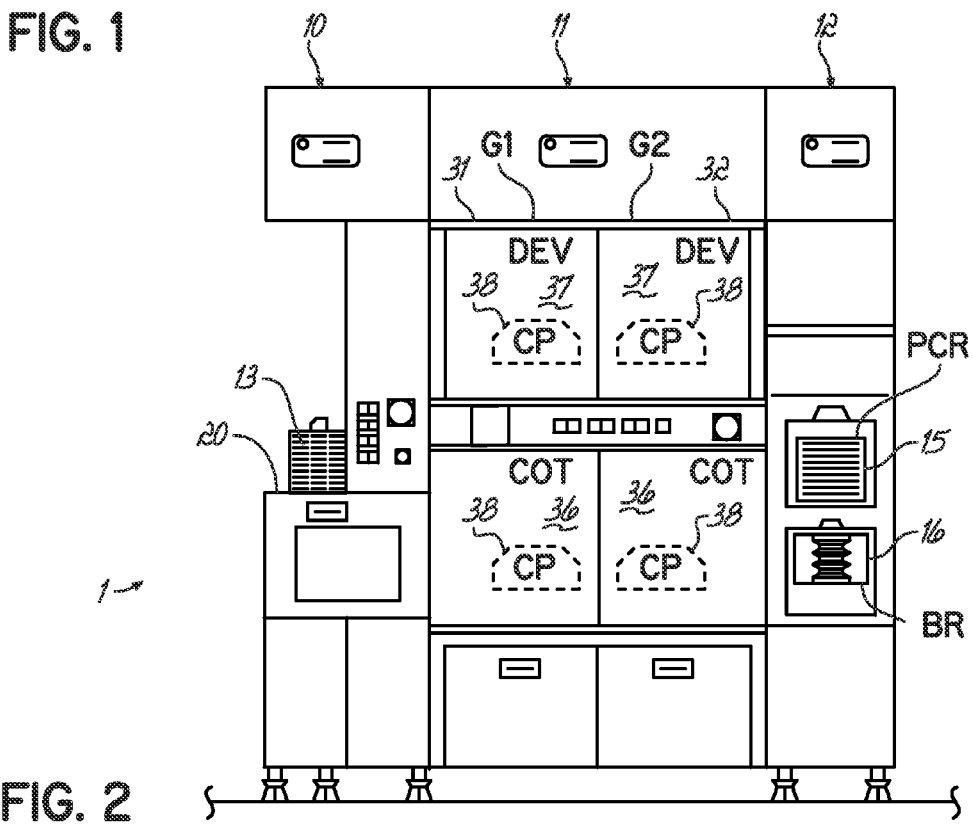
FIG. 2 is a front view of the coating/developing system of FIG. 1.
Figure 3:
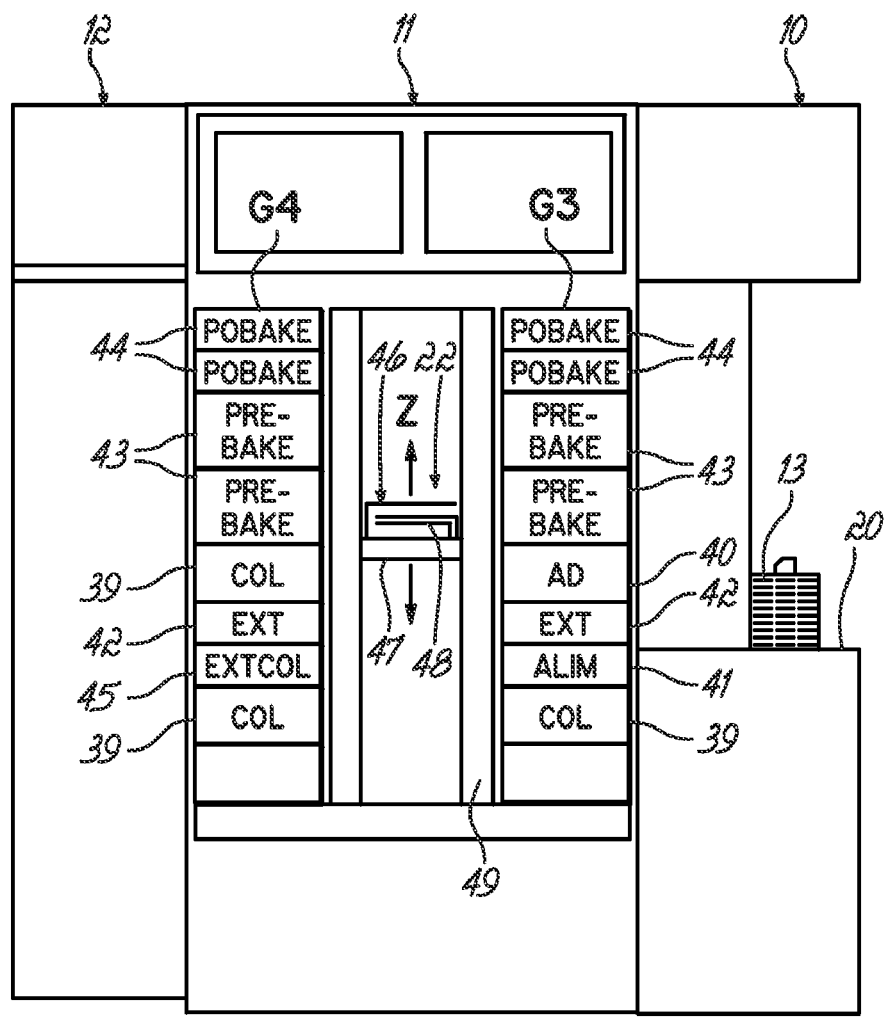
FIG. 3 is a partially cut-away back view of the coating/developing system of FIG. 1, as taken along line 3-3.

With reference to FIGS. 1-3, a coating/developing processing system 1 has a load/unload section 10, a process section 11, and an interface section 12. The load/unload section 10 has a cassette table 20 on which cassettes (CR) 13, each storing a plurality of semiconductor wafers (W) 14 (e.g., 25), are loaded and unloaded from the processing system 1. The process section 11 has various single wafer processing units for processing wafers 14 sequentially one by one. These processing units are arranged in predetermined positions of multiple stages, for example, within first (G1), second (G2), third (G3), fourth (G4) and fifth (G5) multiple-stage process unit groups 31, 32, 33, 34, 35. The interface section 12 is interposed between the process section 11 and one or more light exposure systems (not shown), and is configured to transfer resist coated wafers between the process section. The one or more light exposure system can include a resist patterning system such as a photolithography tool that transfers the image of a circuit or a component from a mask onto the resist on the wafer surface.

The coating/developing processing system 1 also includes a CD metrology system for obtaining CD metrology data from test areas on the patterned wafers. The CD metrology system may be located within the processing system 1, for example at one of the multiple-stage process unit groups 31, 32, 33, 34, 35. The CD metrology system can be a light scattering system, such as an optical diffraction profilometry (ODP) system. The ODP system may include a scatterometer, incorporating beam profile ellipsometry (ellipsometer) and beam profile reflectometry (reflectometer), commercially available from Therma-Wave, Inc. (1250 Reliance Way, Fremont, Calif. 94539) or Nanometrics, Inc. (1550 Buckeye Drive, Milpitas, Calif. 95035). ODP software is available from Timbre Technologies Inc. (2953 Bunker Hill Lane, Santa Clara, Calif. 95054).

When performing optical metrology, such as scatterometry, a structure on a substrate, such as a semiconductor wafer or flat panel, is illuminated with electromagnetic (EM) radiation, and a diffracted signal received from the structure is utilized to reconstruct the profile of the structure. The structure may include a periodic structure, or a non-periodic structure. Additionally, the structure may include an operating structure on the substrate (i.e., a via or contact hole, or an interconnect line or trench, or a feature formed in a mask layer associated therewith), or the structure may include a periodic grating or non-periodic grating formed proximate to an operating structure formed on a substrate. For example, the periodic grating can be formed adjacent a transistor formed on the substrate. Alternatively, the periodic grating can be formed in an area of the transistor that does not interfere with the operation of the transistor. The profile of the periodic grating is obtained to determine whether the periodic grating, and by extension the operating structure adjacent the periodic grating, has been fabricated according to specifications.

A plurality of projections 20a are formed on the cassette table 20. A plurality of cassettes 13 are each oriented relative to the process section 11 by these projections 20a. Each of the cassettes 13 mounted on the cassette table 20 has a load/unload opening 9 facing the process section 11.

The load/unload section 10 includes a first sub-arm mechanism 21 that is responsible for loading/unloading the wafer W into/from each cassette 13. The first sub arm mechanism 21 has a holder portion for holding the wafer 14, a back and forth moving mechanism (not shown) for moving the holder portion back and forth, an X-axis moving mechanism (not shown) for moving the holder portion in an X-axis direction, a Z-axis moving mechanism (not shown) for moving the holder portion in a Z-axis direction, and a θ (theta) rotation mechanism (not shown) for swinging the holder portion around the Z-axis. The first sub-arm mechanism 21 can gain access to an alignment unit (ALIM) 41 and an extension unit (EXT) 42 belonging to a third (G3) process unit group 33, as further described below.

With specific reference to FIG. 3, a main arm mechanism 22 is liftably arranged at the center of the process section 11. The process units G1-G5 are arranged around the main arm mechanism 22. The main arm mechanism 22 is arranged within a cylindrical supporting body 49 and has a liftable wafer transporting system 46. The cylindrical supporting body 49 is connected to a driving shaft of a motor (not shown). The driving shaft may be rotated about the Z-axis in synchronism with the wafer transporting system 46 by an angle of θ. The wafer transporting system 46 has a plurality of holder portions 48 movable in a front and rear direction of a transfer base table 47.

Units belonging to first (G1) and second (G2) process unit groups 31, 32 are arranged at the front portion 2 of the coating/developing processing system 1. Units belonging to the third (G3) process unit group 33 are arranged next to the load/unload section 10. Units belonging to a fourth (G4) process unit group 34 are arranged next to the interface section 12. Units belonging to a fifth (G5) process unit group 35 are arranged in a back portion 3 of the processing system 1.

With reference to FIG. 2, the first (G1) process unit group 31 has two spinner-type process units for applying a predetermined treatment to the wafer 14 mounted on a spin chuck (not shown) within the cup (CP) 38. In the first (G1) process unit group 31, for example, a resist coating unit (COT) 36 and a developing unit (DEV) 37 are stacked in two stages sequentially from the bottom. In the second (G2) process unit group 32, two spinner type process units such as a resist coating unit (COT) 36 and a developing unit (DEV) 37, are stacked in two stages sequentially from the bottom. In an exemplary embodiment, the resist coating unit (COT) 36 is set at a lower stage than the developing unit (DEV) 37 because a discharge line (not shown) for the resist waste solution is desired to be shorter than a developing waste solution for the reason that the resist waste solution is more difficult to discharge than the developing waste solution. However, if necessary, the resist coating unit (COT) 36 may be arranged at an upper stage relative to the developing unit (DEV) 37.

With reference to FIG. 3, the third (G3) process unit group 33 has a cooling unit (COL) 39, an alignment unit (ALIM) 41, an adhesion unit (AD) 40, an extension unit (EXT) 42, two prebaking units (PREBAKE) 43, and two postbaking units (POBAKE) 44, which are stacked sequentially from the bottom.

Similarly, the fourth (G4) process unit group 34 has a cooling unit (COL) 39, an extension-cooling unit (EXTCOL) 45, an extension unit (EXT) 42, another cooling unit (COL) 39, two prebaking units (PREBAKE) 43 and two postbaking units (POBAKE) 44 stacked sequentially from the bottom.

In an exemplary embodiment, the cooling unit (COL) 39 and the extension cooling unit (EXTCOL) 45, to be operated at low processing temperatures, are arranged at lower stages, and the prebaking unit (PREBAKE) 43, the postbaking unit (POBAKE) 44 and the adhesion unit (AD) 40, to be operated at high temperatures, are arranged at the upper stages. With this arrangement, thermal interference between units may be reduced. Alternatively, these units may have different arrangements.

At the front side of the interface section 12, a movable pick-up cassette (PCR) 15 and a non-movable buffer cassette (BR) 16 are arranged in two stages. At the backside of the interface section 12, a peripheral light exposure system 23 is arranged. The peripheral light exposure system 23 can contain a lithography tool and an optical diffraction profilometry (ODP) system. Alternately, the lithography tool and the ODP system may be remote to and cooperatively coupled to the coating/developing processing system 1. At the center portion of the interface section 12, a second sub-arm mechanism 24 is provided, which is movable independently in the X and Z directions, and which is capable of gaining access to both cassettes (PCR) 15 and (BR) 16 and the peripheral light exposure system 23. In addition, the second sub-arm mechanism 24 is rotatable around the Z-axis by an angle of θ and is designed to be able to gain access not only to the extension unit (EXT) 42 located in the fourth (G4) processing unit 34 but also to a wafer transfer table (not shown) near the light exposure system (not shown).

In the processing system 1, the fifth (G5) processing unit group 35 may be arranged at the back portion 3 of the backside of the main arm mechanism 22. The fifth (G5) processing unit group 35 may be slidably shifted in the Y-axis direction along a guide rail 25. Since the fifth (G5) processing unit group 35 may be shifted as mentioned, maintenance operation may be applied to the main arm mechanism 22 easily from the backside.

Figure 4:
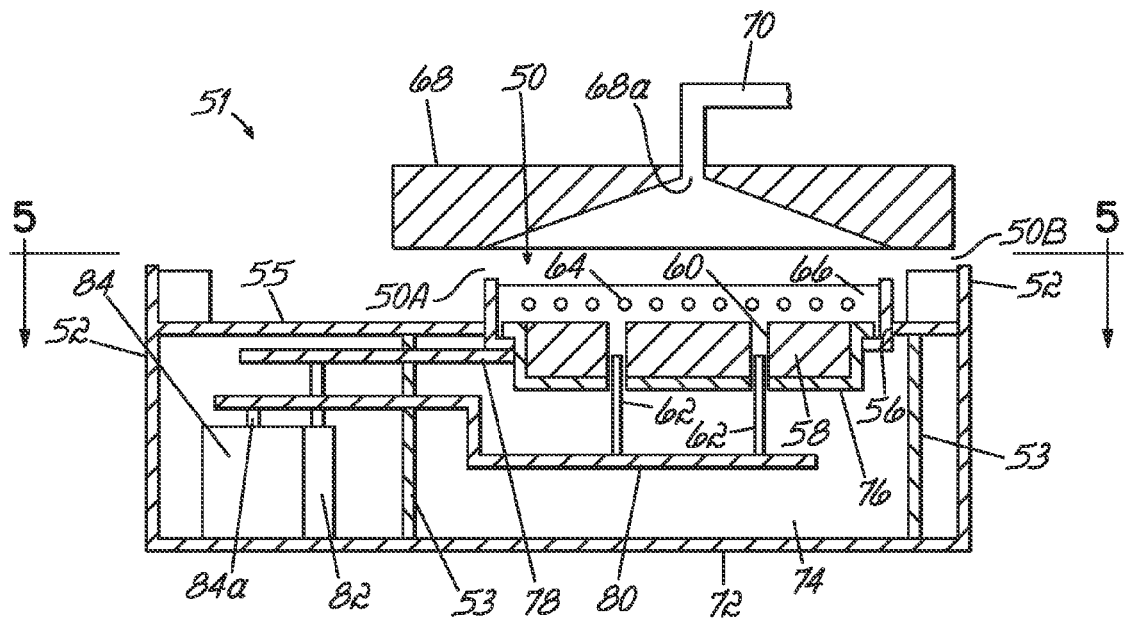
FIG. 4 is a cross-sectional view of a single heat treatment system of FIG. 3.
Figure 5:
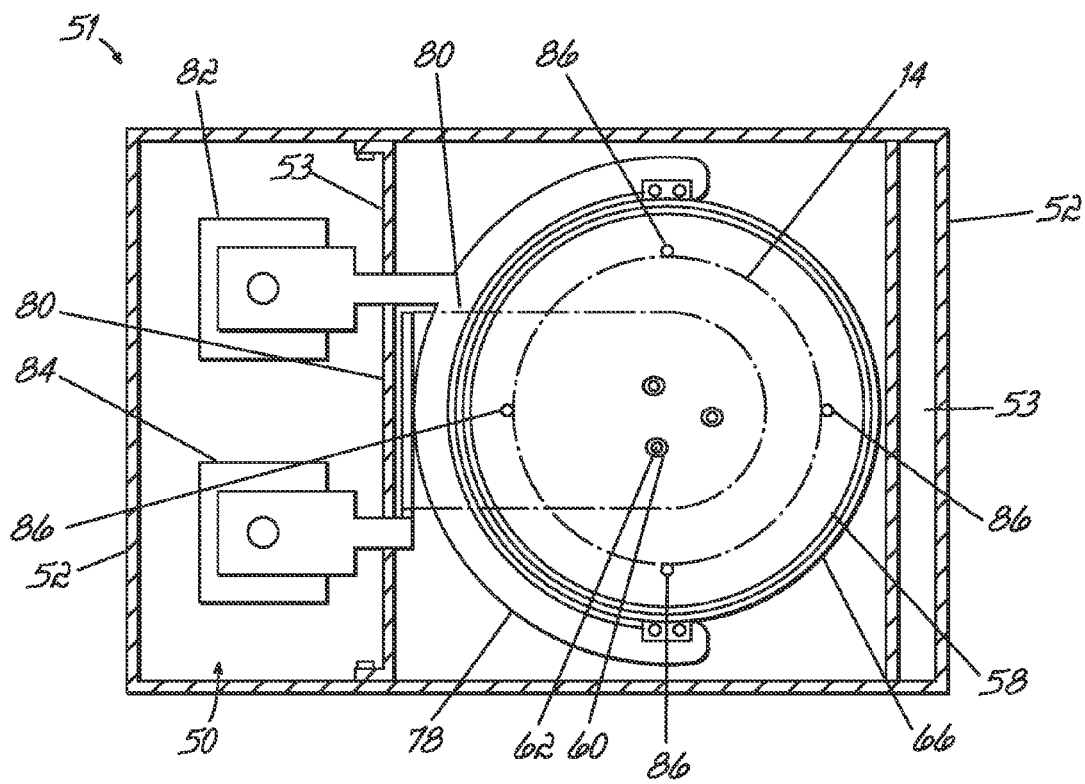
FIG. 5 is a plan view of the heat treatment system of FIG. 4, as viewed from line 5-5.

The prebaking unit (PREBAKE) 43, the postbaking unit (POBAKE) 44, and the adhesion unit (AD) 40 each comprise a heat treatment system in which wafers 14 are heated to temperatures above room temperature. With reference to FIGS. 4 and 5, each heat treatment system 51 includes a processing chamber 50, a hotplate 58, and a resistance heater (not shown) embedded in the hotplate 58.

The hotplate 58 has a plurality of through-holes 60 and a plurality of lift pins 62 inserted into the through-holes 60. The lift pins 62 are connected to and supported by an arm 80, which is further connected to and supported by a rod 84a of a liftable vertical cylinder 84. When the rod 84a is actuated to protrude from the vertical cylinder 84, the lift pins 62 protrude from the hotplate 58, thereby lifting the wafer 14.

With continued reference to FIGS. 4 and 5, the processing chamber 50 is defined by a sidewall 52, a horizontal shielding plate 55, and a cover 68. Openings 50A, 50B are formed at a front surface side (aisle side of the main arm mechanism 22) and a rear surface side of the processing chamber 50, respectively. The wafer 14 is loaded into and unloaded from the processing chamber 50 through the openings 50A, 50B. A circular opening 56 is formed at the center of the horizontal shielding plate 55. The hotplate 58 is housed in the opening 56. The hotplate 58 is supported by the horizontal shielding plate 55 with the aid of a supporting plate 76.

A ring-form shutter 66 is attached to the outer periphery of the hotplate 58. Air holes 64 are formed along the periphery of the shutter 66 at intervals of central angles of two degrees. The air holes 64 communicate with a cooling gas supply source (not shown).

The shutter 66 is liftably supported by a cylinder 82 via a shutter arm 78. The shutter 66 is positioned at a place lower than the hotplate 58 at non-operation time, whereas, at an operation time, shutter 66 is lifted up to a position higher than the hotplate 58 and between the hotplate 58 and the cover 68. When the shutter 66 is lifted up, a cooling gas, such as nitrogen gas or air, is exhausted from the air holes 64.

With reference to FIG. 4, an exhaust port 68a at the center of the cover 68 communicates with an exhaust pipe 70. Gas generated from the surface of the wafer 14 at the heat treatment detected temperature time is exhausted through the exhaust port 68a and vented from the processing chamber 50 via exhaust pipe 70 to an evacuation unit (not shown).

With reference to FIGS. 4 and 5, a compartment 74 is defined by the horizontal shielding plate 55, two sidewalls 53, and a bottom plate 72 formed below the horizontal shielding plate 55. Hotplate supporting plate 76, shutter arm 78, lift pin arm 80, and liftable cylinders 82, 84 are arranged in the compartment 74.

With reference to FIG. 5, a plurality of projections 86 are formed on an upper surface of the hotplate 58 for accurately positioning the wafer 14. In addition, a plurality of smaller projections (not shown) is formed on the upper surface of the hotplate 58. When the wafer 14 is mounted on the hotplate 58, top portions of these smaller projections contact the wafer 14, which produces a small gap between the wafer 14 and the hotplate 58 that prevents the lower surface of the wafer 14 from being strained and damaged.

Figure 6:
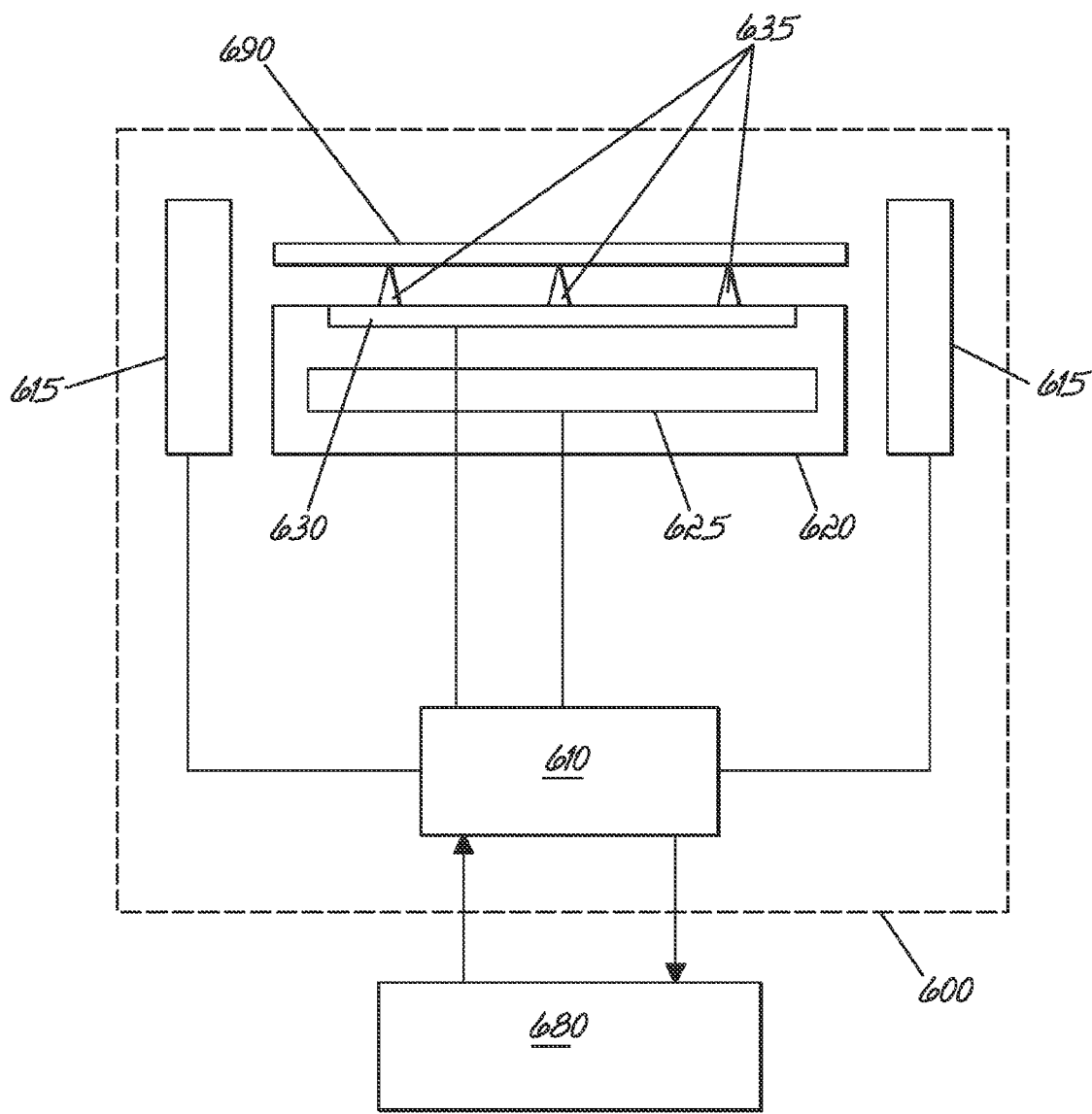
FIG. 6 is a diagrammatic view of a hotplate of a heat treatment system in accordance with an embodiment of the invention.

With reference to FIG. 6, a heat treatment system 600 in accordance with an embodiment of the invention includes a controller 610, a ventilation system 615, and a hotplate 620. Hotplate 620 includes a heater 625, a sensor 630, and wafer support pins 635. A wafer 690 may be positioned on hotplate 620 using wafer support pins 635.

Hotplate 620 may have a circular shape and may comprise a number of segments (not shown). In addition, heater 625 may comprise a number of heating elements (not shown). For example, a heating element may be positioned within each segment of the hotplate 620. In an alternate embodiment, hotplate 620 may incorporate a cooling element and/or a combined heating/cooling element rather than a heating element.

Hotplate 620 may include a sensor 630, which may be a physical sensor and/or a virtual sensor. For example, sensor 630 may be a temperature sensor located within each hotplate segment. In addition, sensor 630 may include at least one pressure sensor. Controller 610 may be coupled to heater 625 and sensor 630. Various types of physical temperature sensors 630 may be used. For example, the sensors 630 can include a thermocouple, a temperature-indicating resistor, a radiation type temperature sensor, and the like. Other physical sensors 630 include contact-type sensors and non-contact sensors.

Heat treatment system 600 may be coupled to a processing system controller 680 capable of providing data for an incoming wafer to heat treatment system 600. The data can include wafer information, layer information, process information, and metrology information. Wafer information can include composition data, size data, thickness data, and temperature data. Layer information can include the number of layers, the composition of the layers, and the thickness of the layers. Process information can include data concerning previous steps and the current step. Metrology information can include optical digital profile data, such as critical dimension (CD) data, profile data, and uniformity data, and optical data, such as refractive index (n) data and extinction coefficient (k) data. For example, CD data and profile data can include information for features and open areas in one or more layers, and can also include uniformity data.

Figure 13:
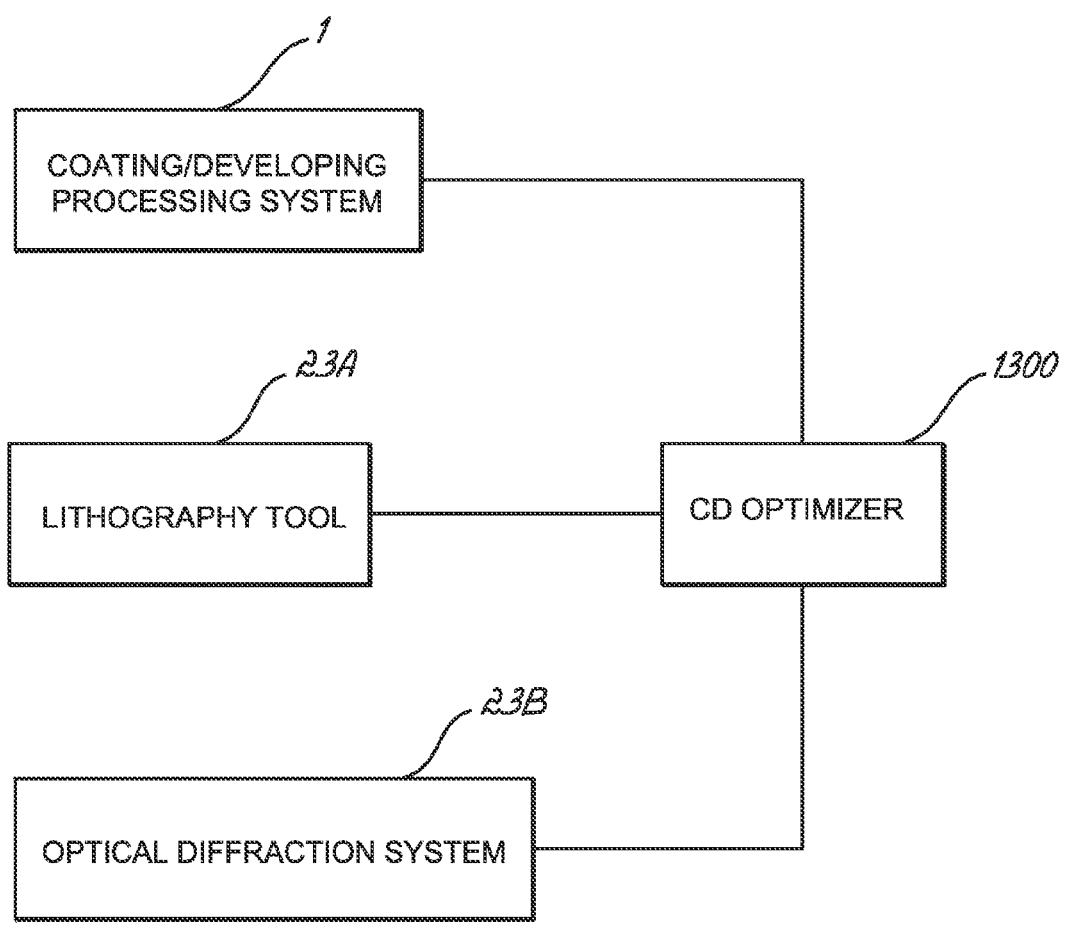
FIG. 13 schematically shows a CD optimizer system coupled to a coating/developing system, a lithography tool, and an optical diffraction system according to an embodiment of the invention.

Controller 610 may control the temperature of each of the plurality of hotplate segments (control zones) to establish a temperature profile for the hotplate surface. The controller 610 may receive instructions from a CD optimizer system 1300 depicted in FIG. 13 to adjust the temperature of the plurality of hotplate segments based on CD metrology data received from heat-treated wafers. The CD optimizer system 1300 may be contained in the processing system controller 680 or the CD optimizer system 1300 may be contained in the controller 610. Adjusting the temperature of the plurality of hotplate segments establishes an adjusted temperature profile for the hotplate surface for heat-treating additional resist coated wafers.

Controller 610 may comprise a microprocessor, a memory (e.g., volatile and/or non-volatile memory), and a digital I/O port. A program stored in the memory may be utilized to control the aforementioned components of a heat treatment system according to a process recipe. Controller 610 may be configured to analyze the process data, to compare the process data with target process data, and to use the comparison to change a process and/or control the processing system components.

A ventilation system 615 is provided around the hotplate 620. Air or nitrogen gas may be provided to one or more surfaces of the hotplate 620 by ventilation system 615. For example, a shutter 66 and air holes 64 (FIG. 5) may be used. The ventilation system 615 can communicate with a gas supply source (not shown) at the upstream. Controller 610 can control the flow rate of gas flowing from the ventilation system 615. In an alternate embodiment, heat treatment system 600 may include a monitoring device (not shown) that, for example, permits optical monitoring of the wafer.

Figure 7A:
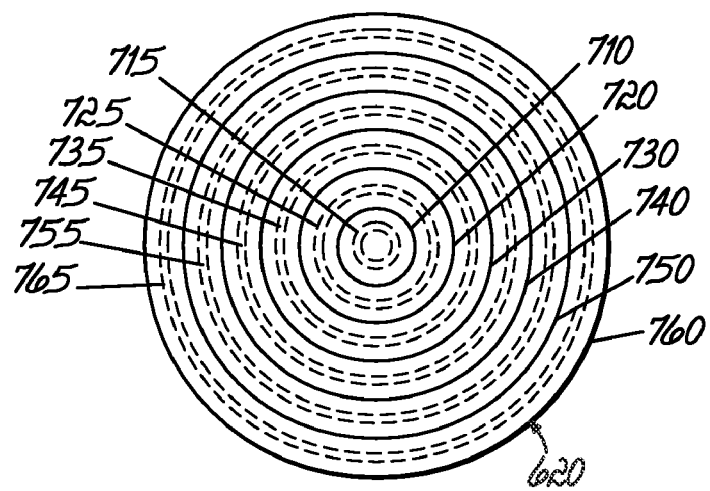
FIGS. 7A and 7B are diagrammatic views of hotplates in accordance with embodiments of the invention.
Figure 7B:
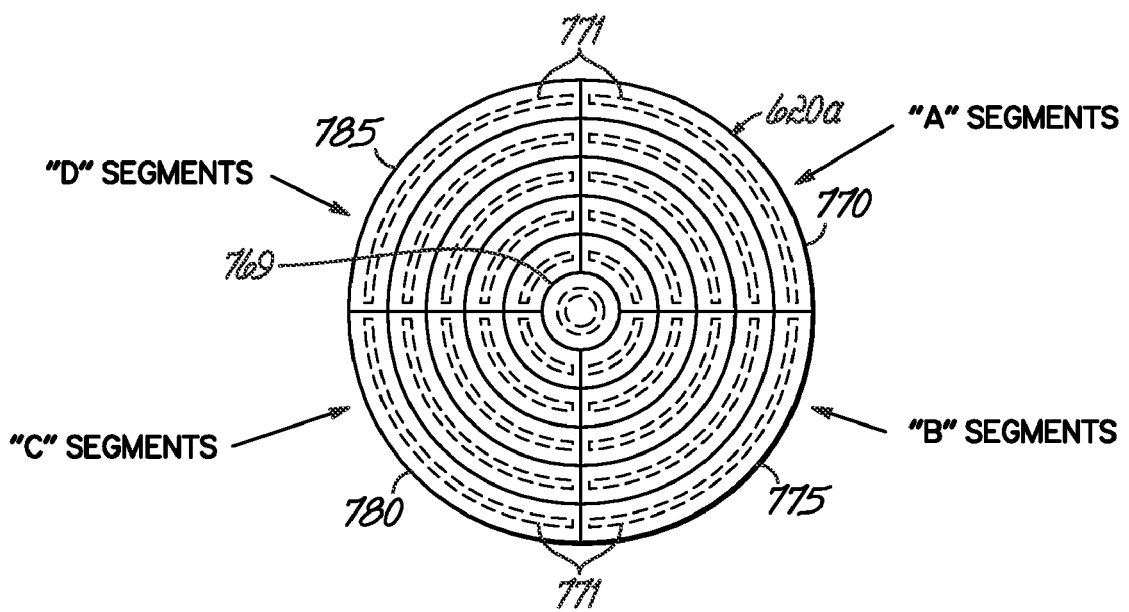

FIGS. 7A and 7B show exemplary schematic views of hotplates in accordance with an embodiment of the invention. In FIG. 7A, a circular hotplate 620 has a circular segment 710 and a plurality of annular ring segments 710, 720, 730, 740, 750, and 760. Hotplate 620 may include any number of segments, which may have any suitable geometrical arrangement and/or dimensions. For example, the annular ring segments may have different radial dimensions relative to the hotplate centerline. In the illustrated embodiment, each segment 720, 730, 740, 750, and 760 includes a corresponding one of a plurality of heating elements 715, 725, 735, 745, 755, and 765, each of which may be independently controlled.

With reference to FIG. 7B, a circular hotplate 620a has a circular central segment 769 and a plurality of sectors 770, 775, 780, 785. Equal radial dimension segments A, B, C, D are shown in FIG. 7B, but this is not required for the invention. Hotplate 620a may include any number of sectors and segments, which may have any suitable geometrical arrangement and/or dimensions. In the illustrated embodiment, individual segments A, B, C and D in sectors 770, 775, 780, 785 and central segment 769 each include at least one of a plurality of heating elements 771 that may each be independently controlled.

Figure 8:
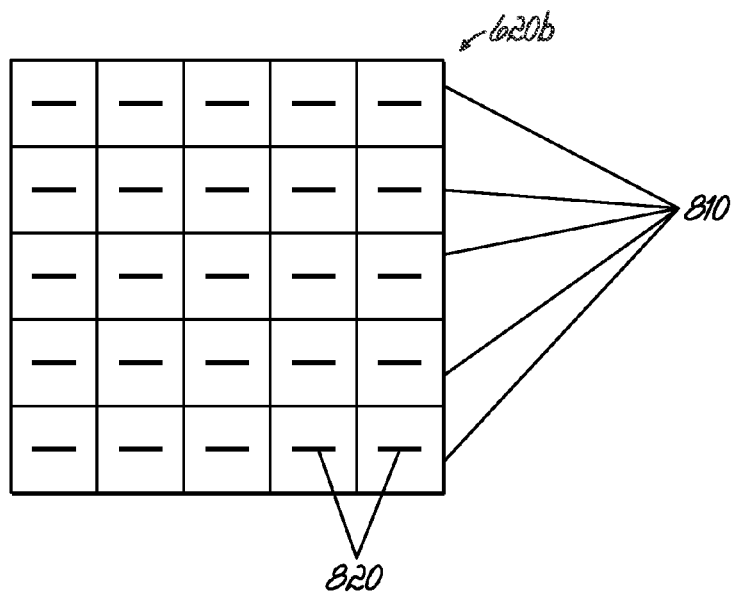
FIG. 8 is a diagrammatic view of a hotplate in accordance with an alternative embodiment of the invention.

FIG. 8 shows a schematic view of another hotplate 620b, in accordance with an embodiment of the invention, having a plurality of, for example, twenty-five square segments 810. Hotplate 620b may comprise a different number of segments 810, and the segments 810 may be shaped differently. For example, rectangular shapes may be used. In the illustrated embodiment, each segment 810 of the hotplate 620b includes a heating element 820, and each heating element 820 may be independently controlled.

Alternately, any of hotplates 620 and 620a-b may be constructed in the jacket form having at least one hollow and at least one recess. The wafer 690 (FIG. 6) may be heated by circulating a heat medium to the recesses, such as by inserting a heater or a heat pipe (not shown) into one or more recesses containing a liquid (heat medium). Alternatively, the hotplate may be heated to a predetermined heat treatment temperature by allowing at least one hollow to be filled with vapor generated from a heat medium by application of heat thereto at one or more of the recesses.

Figure 9:
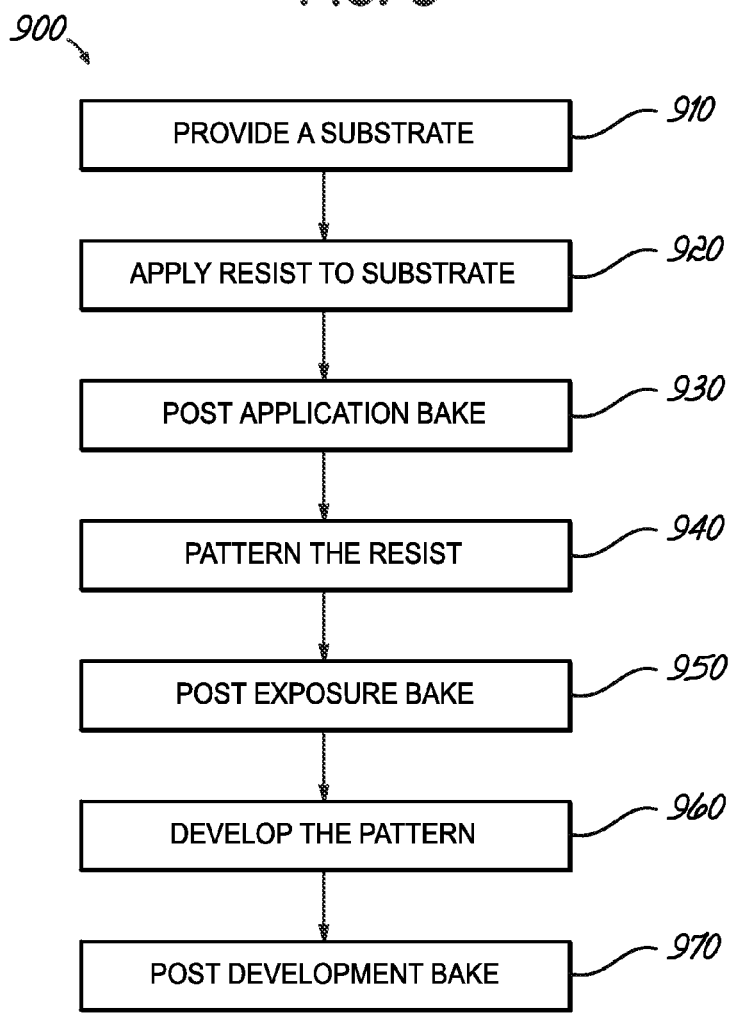
FIG. 9 is a simplified process flow diagram for a method of patterning a resist coated wafer according to an embodiment of the invention.

FIG. 9 is a simplified process flow diagram for a method of patterning a resist coated wafer according to embodiments of the invention. The patterning process produces a pattern that covers portions of the wafer with a resist. For example, during a photolithography process, complex circuit patterns are imaged onto the photosensitive resist material by a lithography tool to provide a physical barrier during further processing of the wafer to form semiconductor devices. During the further processing, the lithographic pattern can be transferred into the underlying wafer or wafer layers by an etching process (e.g., a plasma etching process) that includes selective removal of wafer material not covered by resist.

The process 900 represents a typical process to which embodiments of the invention can be applied. Referring also to FIGS. 1-3 and 13, starting at 910, a wafer is provided in coating/developing processing system 1 depicted in FIGS. 1-3.

In 920, a resist is applied to the wafer. For example, the resist material can be applied by dispensing a liquid containing the resist material onto the wafer while the wafer is mounted on a spin chuck (not shown) with a cup (not shown). For example, the resist can be a chemically amplified resist (CAR). A CAR can be characterized by an acid component, a quenched component, and an inhibitor quencher. In one example, an adhesion layer or a surfactant layer can be provided on the wafer surface before the resist material is applied.

CARs were developed to enhance the exposure process because of the low spectral energy of deep ultraviolet (DUV) radiation. A CAR contains one or more components that are insoluble in a developer solution. These components can comprise chemical protectors. A CAR can also contain a photoacid generator (PAG). During a radiation exposure step, the PAGs produce acid molecules for the patterning process. Desirably, the acid molecules remain inactive until a post exposure bake (PEB) is performed. The PEB drives a de-protection reaction forward in which the thermal energy causes the acid to react with the chemical protectors.

In 930, a post application bake (PAB) can be performed in the coating/developing processing system 1 to cure the applied resist. In an alternate embodiment, a curing step is not required. In addition, a cooling step can be performed after the PAB. In a PAB heating unit, the resist can be heated to temperatures at least higher than room temperature, and in a cooling unit, the resist, can be cooled to temperatures at or below room temperature.

In 940, the resist is patterned in a lithography tool 23A using light radiation or charged particles such as electrons. The desired pattern can, for example, be created on the resist using beams of high-energy electrons or arrays of laser beams and a mask that defines the size and shape of the pattern. For example, deep ultraviolet (DUV) can be used. DUV lithography is a key enabling technology that can be used to manufacture semiconductor devices with features of 0.25 microns (micron=$10^{-6}$ m) or less.

In other cases, extreme ultraviolet (EUV) sources can be used for critical dimensions below 0.05 microns. EUV lithography utilizes light with wavelengths in a range of about 5 nm to 50 nm, with about 13 nm being the most common.

In 940, the resist pattern is exposed to the light radiation or charged particles for a predetermined time period to achieve a desired exposure dose. Exposure dose refers to the amount of energy (per unit area) that the resist is subjected to upon exposure by the lithography tool 23A. For optical lithography, exposure dose is equal to the light intensity times the exposure time. In resist patterning, resolution is the smallest feature that can be printed (e.g., for a given process and processing system) with sufficient quality. It is common to use focus and exposure dose as process variables, so that resolution is defined as the smallest feature of a given type that can be printed with a specified depth of focus. The depth of focus of a feature is often defined as the range of focus that keeps the resist profile of a given feature within all specifications (e.g., linewidth, sidewall angle, resist loss) over a specified exposure range.

The lithography tool 23A can contain a controller (not shown) to control the exposure dose and focus across a wafer to be patterned. The controller may receive instructions from the CD optimizer system 1300 to adjust the exposure dose and focus based on CD metrology data received from the patterned wafers. Adjusting the exposure dose and focus of the lithography tool 23A establishes adjusted exposure dose and focus settings across the wafer for patterning additional resist coated wafers.

In 950, a PEB process can be performed in the coating/developing processing system 1 to drive the de-protection reaction forward. The de-protection reaction is acid driven and takes place in the areas exposed to the radiation or to the charged particles. In addition, a cooling step can be performed after the PEB. In a PEB heating unit, the resist can be heated to temperatures at least higher than room temperature, and in a cooling unit, the resist can be cooled to temperatures at or below room temperature.

The PEB process plays an important role in the process 900. Heat-treating a resist can have many purposes that range from removing a solvent from the resist material to catalyzing the chemical amplification. In addition to the intended results, heat-treating can cause numerous problems. For example, the light or charged particle sensitive component of the resist may decompose at temperatures typically used to remove the solvent, which is an extremely serious concern for a chemically amplified resist since the remaining solvent content has a strong impact on the diffusion and amplification rates. Also, heat-treating can affect the dissolution properties of the resist and thus have direct influence on the developed resist profile.

In 960, the resist is developed in the coating/developing processing system 1 by selectively dissolving exposed areas of the resist. For example, a developing solution, such as a 2.3 wt % solution of tetramethyl ammonium hydroxide (TMAH), can be used. In addition, rinsing steps can also be performed. For example, a developing solution and/or a rinsing solution can be applied by mounting the wafer on a spin chuck (not shown) within a cup (not shown).

In 970, a post development bake (PDB) can be performed in the coating/developing processing system 1 to harden the resist pattern in preparation for subsequent pattern transfer into the underlying wafer or wafer layers. For example, the post development bake can improve the etch resistance of the patterned resist during plasma etching of the underlying wafer.

Following formation of a patterned resist, a critical dimension (CD) of the patterned resist may be inspected by the optical diffraction system 23B at a plurality of test areas on the wafer to determine if it has been correctly manufactured. CD commonly refers to a size (width) of a feature formed in the resist. Key requirements for the processing of wafers are tight CD control, tight profile control, and tight uniformity control—both within a wafer and wafer to wafer. For example, variations in CD measurements, profile measurements, and uniformity measurements are commonly caused by variations in temperature profile across a wafer and variations in thermal response from wafer to wafer.

The CD metrology data that is obtained contains important information on the CD and the CD uniformity of the patterned resist at the inspected test areas across the wafer. The CD metrology data obtained by the inspection process may be utilized to reduce CD variations due to variations in light exposure and focus settings during an exposure step and temperature-related variations during a heat-treating step such as the PEB step.

The CD metrology data from optical diffraction system 23B may be relayed to the CD optimizer system 1300. The CD optimizer system 1300 can provide adjusted exposure dose and focus settings for wafers to be exposed in the lithography tool 23A and adjusted temperature profile for wafers to be heat-treated in the coating/developing processing system 1, in order to reduce CD variations in the subsequently heat-treated wafers. The CD optimizer can utilize an exposure model for real time correction to adjust the exposure dose and focus settings of the lithography tool 23A across a wafer to improve CD uniformity and thermal model for real time correction to adjust the temperature profile of the hotplate surface to improve CD uniformity due to variations in temperature profile across a wafer. The heat-treating can be performed using a hotplate system having multiple temperature control zones, and the hotplate system has feedback and feed-forward controllers to manipulate the hotplate temperature field and the temperature profile across a wafer.

A common problem encountered when inspecting CDs at a plurality of test areas on a patterned/heat-treated wafer arises from the necessity and/or desire to inspect a large number of test areas on the wafer to obtain high CD metrology data density across the wafer for good CD optimization. However, the relatively long inspection times required for obtaining high CD metrology data density on each patterned wafer can directly limit the wafer throughput of the coating/developing processing system 1. In one example, a desired wafer throughput of 120 wafers per hour (wph) may only allow for obtaining CD metrology data at 5 different test areas on each patterned/heat-treated wafer. However, it may be necessary and/or desired to obtain CD metrology data at many more test areas for good CD optimization. Thus, a wafer throughput of 120 wph may not be possible if CD metrology data is obtained at more than 5 test areas on each wafer.

Embodiments of the invention provide a method for obtaining high CD metrology data density while also allowing for high wafer throughput. Embodiments of the invention provide real time dynamic CD control that provides high CD metrology data density for CD control and optimization to reduce the critical dimension (CD) variations, reduce the feature profile variations, and reduce the uniformity variations across a patterned resist on a wafer. CD and profile measurements can apply to trenches, vias, and other features.

According to one embodiment of the invention, CD metrology data is obtained from a plurality of test areas on each processed wafer, where different groups of test areas are selected for two or more of the processed wafers. The different groups of test areas have a different position for one or more of the test areas on the wafer relative to the other processed wafers. The CD metrology data obtained for each processed wafer is overlaid to construct a CD metrology data map with high CD metrology data density across the wafer for good CD optimization. This allows for obtaining the desired CD metrology data density across the wafer while achieving the desired wafer throughput of the coating/developing processing system 1.

According to one embodiment of the invention, CD metrology data may be obtained from "m" number of test areas on each of "N" number of processed wafers, where m and N are integers. The position of each test area on a processed wafer may be determined relative to a wafer marker, such as an alignment notch at the wafer edge. A CD metrology data map may be constructed from the CD metrology data from the m×N test areas. If there are "y" total number of repeated tests (i.e., CD metrology data obtained from the same test position (e.g., wafer center) on different processed wafers), then the number of different test areas ($m_{map}$) on the CD metrology data map can be expressed as:

$$m_{map} = mN - y \quad (1)$$

For a heat-treating system containing a plurality of hot plates, equation (1) may be written as:

$$m_{i(map)} = mN_i - y_i \; i=1, 2, 3, \ldots \quad (2)$$

where i is the hot plate index, $N_i$ is the number of wafers processed by hotplate i, and $y_i$ is the total number of repeated tests performed on wafers processed by hot plate i.

For a desired number of different test areas $m_{map}$ on a CD metrology data map, several combinations of m, N, and y may be determined using Equations (1) and (2). Furthermore, the throughput of the coating/developing processing system 1 may be determined for the different combinations of m, N, and y, and compared to the desired throughput. If a predetermined combination of m, N, and y does not yield the desired wafer throughput, one or more of m, N, and y may be changed to achieve the desired wafer throughput.

Figure 10A:
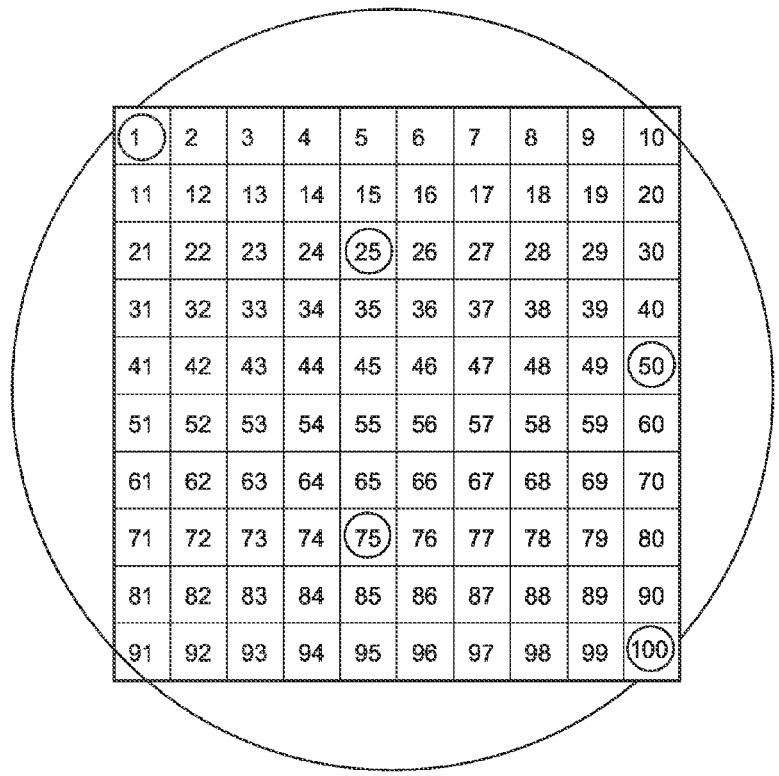
FIGS. 10A-10D schematically show different groups of test areas for acquiring CD metrology data according to an embodiment of the invention.
Figure 10B:
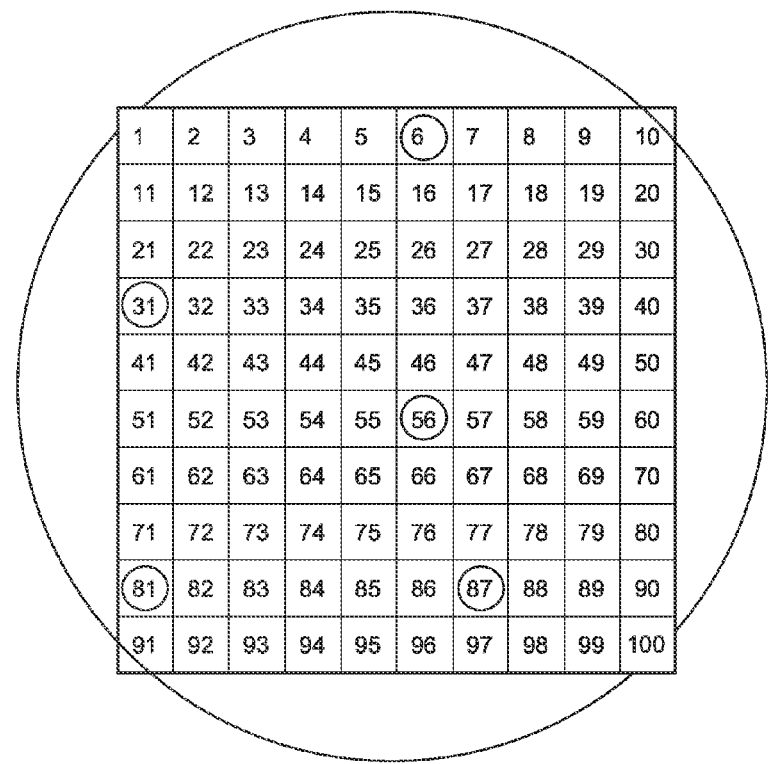
Figure 10C:
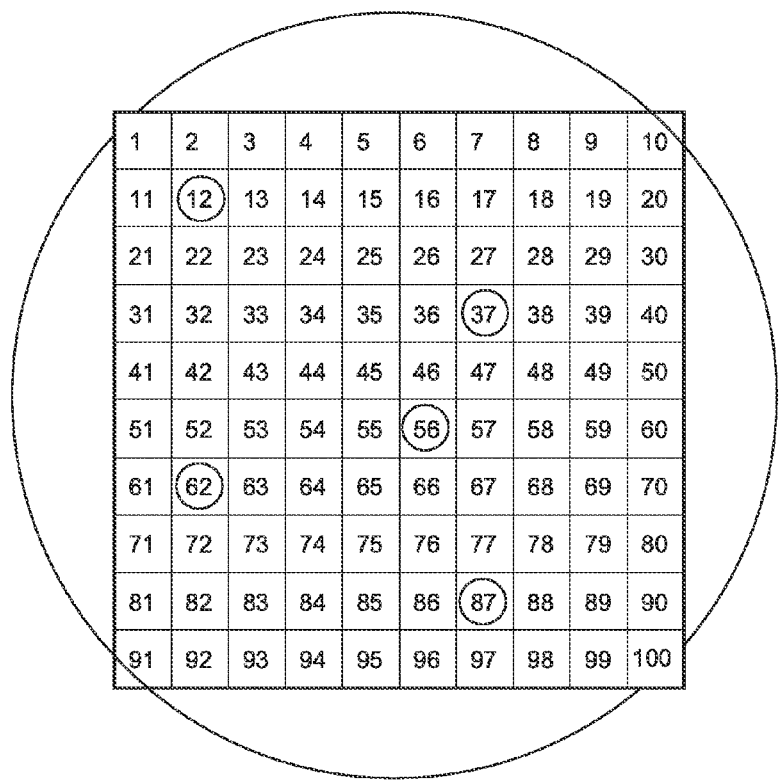
Figure 10D:
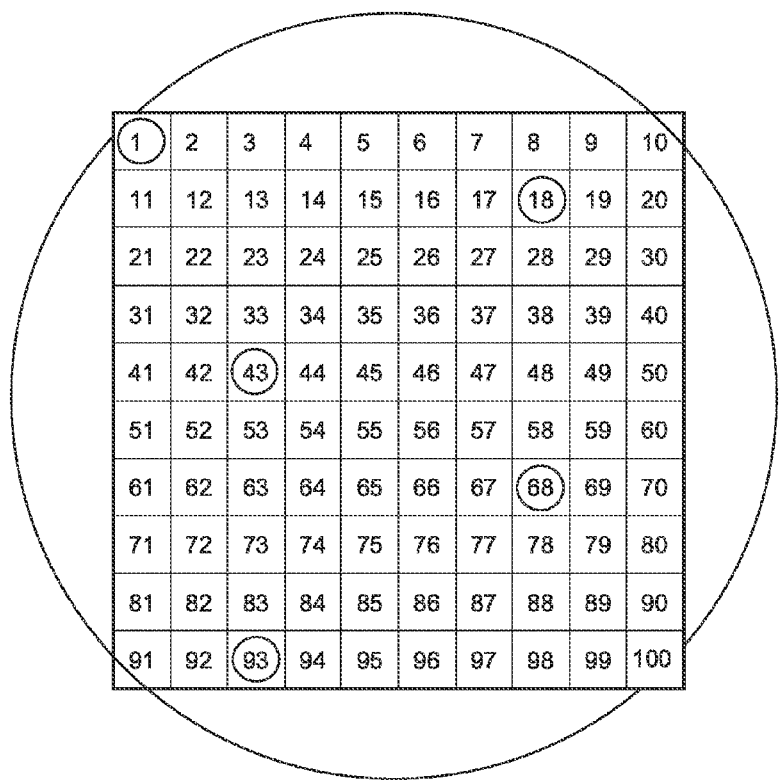
Figure 10E:
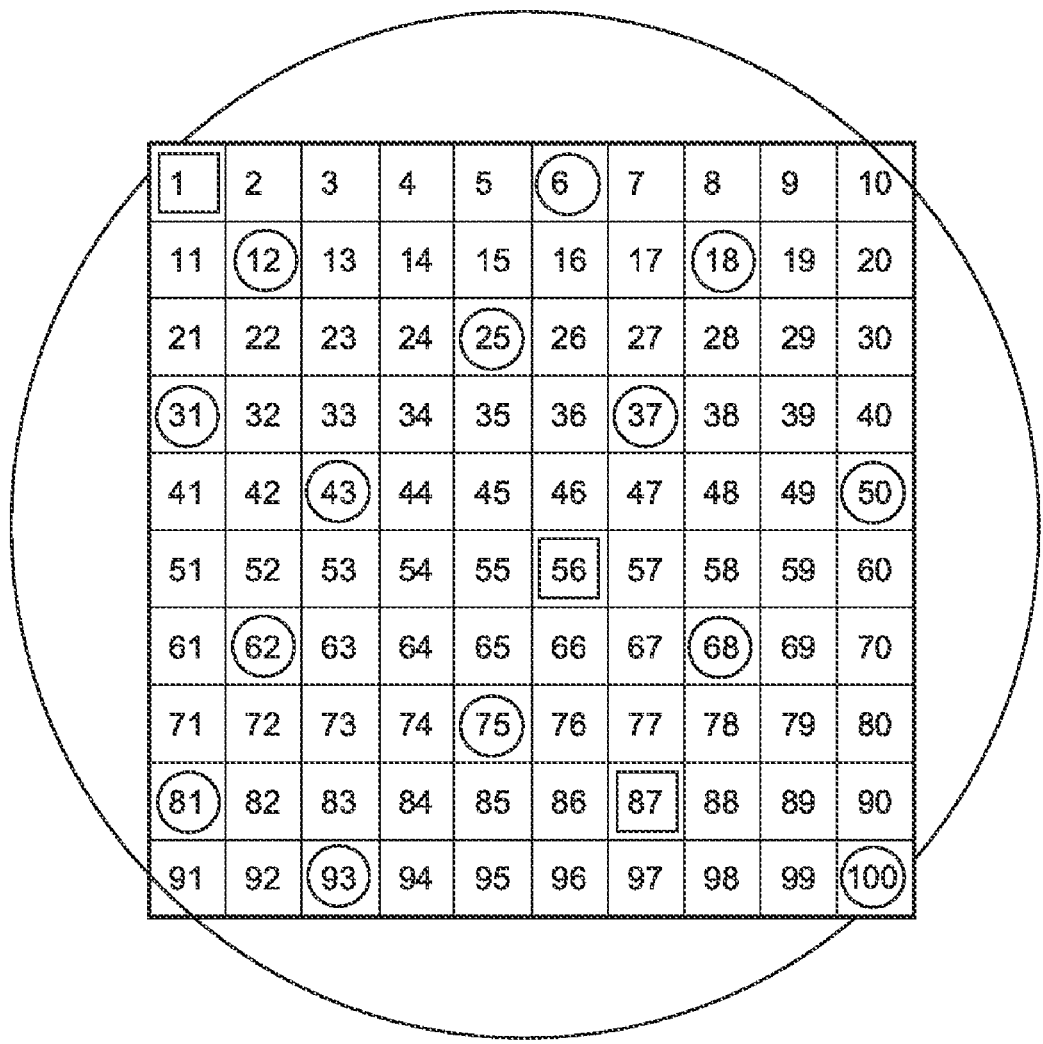
FIG. 10E schematically shows a CD metrology data map constructed from the different groups of test areas in FIGS. 10A-10D according to an embodiment of the invention.

FIGS. 10A-10D schematically show different groups of test areas for acquiring CD metrology data and FIG. 10E schematically shows a CD metrology data map constructed from the different groups of test areas in FIGS. 10A-10D according to one embodiment of the invention. In an example of one embodiment, a 10×10 grid of test areas is constructed and a series expansion of the 100 test areas is used to select 5 test areas, indicated by open circles, for each of the 4 processed wafers. The total number of repeated tests "y" is indicated by open squares in FIG. 10E, and in this example, y=3. Using equation (1) for m=5, N=4, and y=3, the CD metrology map in FIG. 10E has $m_{map}=17$.

In another example, a CD metrology data map containing 33 or more different test areas may be desired for good CD optimization. A CD metrology data map with $m_{map}=33$ may be achieved by selecting m, N, and y as 5, 8, and 7, respectively. In this example, 5 test areas are inspected on the 8 processed wafers with a total of 7 repeated tests.

In yet another example, a CD metrology data map with $m_{map}=35$ may be achieved by selecting m, N, and y as 5, 7, and 0, respectively. In this example, 5 test areas are inspected on the 7 processed wafers with no repeated tests.

According to embodiments of the invention, any combination of m, N, and y may be used that result in the desired wafer throughput. In general, the higher the desired wafer throughput, the fewer test areas are inspected on each processed wafer. In practice, the time it takes to make a large number of measurements on each wafer may be too long to achieve the desired throughput of the coating/developing processing system.

According to one embodiment of the invention, a CD metrology data map may be constructed as a cumulative overlay of CD metrology data from all processed wafers inspected. The cumulative overlay at each test area may, for example, be generated as an average or as a weighted average of the CD metrology data obtained. For example, a weighted average may favor most recently processed wafers over earlier processed wafers.

According to another embodiment of the invention, a CD metrology data map may be constructed as a time varying average or a time varying weighted average of the CD metrology data obtained. For example, the CD metrology data map may be constructed as a time varying average or a time varying weighted average of a predetermined number of the most recently processed wafers, where the predetermined number may be selected in view of the CD metrology data density across the wafer required for constructing a CD metrology data map for good CD optimization. For example, a time varying weighted average may favor most recently processed wafers over earlier processed wafers.

Figure 11:
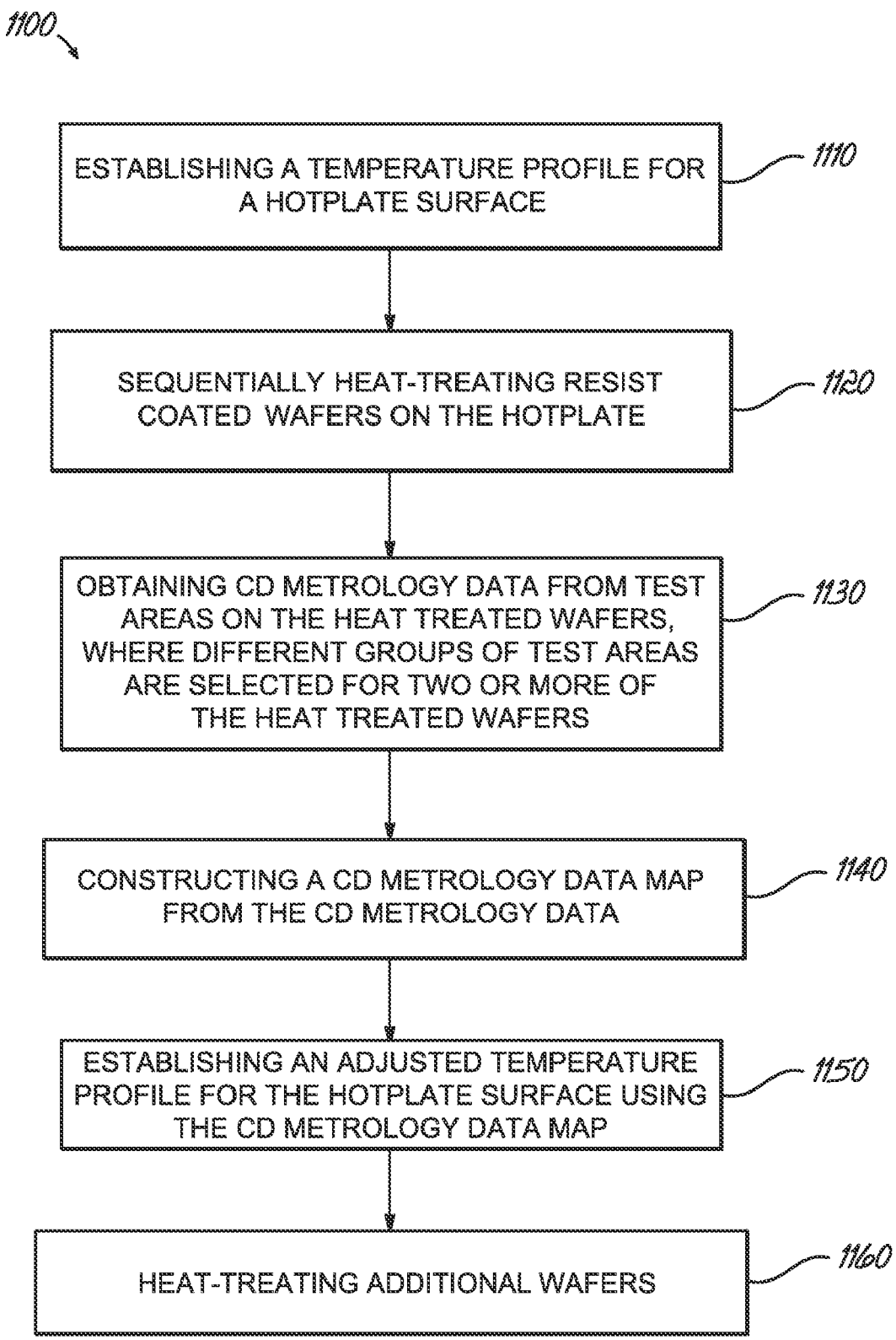
FIG. 11 is a simplified process flow diagram of a method for dynamic CD control and optimization in accordance with an embodiment of the invention.

FIG. 11 is a simplified process flow diagram of a method for dynamic CD control and optimization in accordance with an embodiment of the invention. The process flow 1100 includes, in 1110, establishing a temperature profile for a hotplate surface. The hotplate surface can be divided into a plurality of temperature control zones and substantially equal temperatures can be established for all of the temperature control zones. Alternately, different temperatures can be established for one or more of the temperature control zones. According to an embodiment of the invention, establishing the temperature profile can include establishing a known temperature for each of the plurality of temperature control zones. For example, a temperature profile can be established based on historical data for this type of wafer and resist.

In one embodiment, one or more heater elements are located within each temperature control zone. Alternately, cooling elements can be provided. In addition, one or more temperature sensors can be located within each temperature control zone. Alternately, optical techniques can be used to measure temperature.

In 1120, resist coated wafers are sequentially heat-treated on the hotplate. The heat-treating can, for example, include a PEB process or a PDB process. The PEB process is a thermally activated process and serves multiple purposes in photoresist processing. First, the elevated temperature of the bake drives the diffusion of the photoproducts. A small amount of diffusion may be useful in minimizing the effects of standing waves, which are the periodic variations in exposure dose throughout the depth of the film that result from interference of incident and reflected radiation. The other main purpose of the PEB is to drive an acid-catalyzed reaction that alters polymer solubility in many chemically amplified resists.

Chemical amplification is important because it allows a single photoproduct to cause many solubility-switching reactions, thus increasing the sensitivity of these photoresist systems. Some amount of acid transport is necessary in that it allows a single acid to move to many reactive polymer sites. However, acid transport from nominally exposed to unexposed regions can complicate control of resist feature dimensions. Acid transport through these reactive systems is mechanistically complex. Measurements have shown that there is a very large difference in acid mobility between the starting material, which is reactive towards acid, and the product material, which is no longer reactive.

The CAR reactions may be incorporated into a thermal model to determine the thermal dose at various positions in the wafer during the PEB process. Dose computation may be made by including the ramp up, stabilization, processing, and cool-down portions of the thermal trajectories, and these may be more accurate than simply "at-temperature" calculations.

In 1130, CD metrology data is obtained from test areas on the heat treated wafers. According to embodiments of the invention, different groups of test areas are selected for two or more of the heat-treated wafers. The total number of test areas per wafer may be identical. Alternately, the total number of test areas per wafer may be different. According to one embodiment of the invention, the test areas may form a random pattern on a grid, for example as shown in FIG. 10. According to another embodiment of the invention, the test areas may form a pattern that is rotated a predetermined angle from wafer to wafer. For example, each wafer may be inspected at 5 test areas distributed according to a predetermined pattern over the wafer, where the 5 test area pattern is rotated the predetermined angle from wafer to wafer. In general, the CD metrology data map may have any suitable geometrical arrangement that provides the desired data density across a wafer.

According to one embodiment of the invention, the CD metrology data may be obtained by selecting a desired throughput of heat-treated wafers, and selecting the number of test areas on the heat-treated wafer based on the selected throughput of the heat-treated wafers.

In 1140, a CD metrology data map is constructed from the CD metrology data. The CD metrology data map may be constructed by overlaying the CD metrology data at the different test areas. According to one embodiment of the invention, the CD metrology data map may be constructed as a cumulative average or weighted average of CD metrology data from a predetermined number of heat-treated wafers. According to another embodiment of the invention, the CD metrology data map may be constructed as a cumulative average or weighted average of CD metrology data from a predetermined number of consecutively heat-treated wafers.

In 1150, an adjusted temperature profile is established for the hotplate surface using the CD metrology data map. According to an embodiment of the invention, establishing the adjusted temperature profile can include establishing a second known temperature for each of the plurality of temperature control zones. The CD metrology data map may be forwarded to a CD optimizer system and the temperature profile adjusted based on an output of the CD optimizer. The CD optimizer system can utilize a thermal model for real time correction to adjust the temperature profile of the hotplate surface to improve CD uniformity due to variations in temperature profile across a wafer. The CD optimizer system is configured to adjust the temperature profile using power controllers and temperature sensors that manipulate the hotplate temperature field and the temperature profile across the hotplate surface.

In 1160, when an adjusted temperature profile has been established for the hotplate surface, additional resist coated wafers may be heat-treated on the hotplate. According to one embodiment if the invention, the temperature profile across the hotplate surface may be adjusted between each wafer to be heat-treated on the hotplate. Alternately, the temperature profile across the hotplate surface may be adjusted between a predetermines number of wafers to be heat-treated on the hotplate.

In addition to heat-treating resist coated wafers using a single hotplate, embodiments of the invention may be applied to heat-treating resist coated wafers using a plurality of hotplates. When using a plurality of hotplates, different levels of temperature fluctuations may be observed for the different hotplates. According to one embodiment of the invention, a method is provided for high density CD control and optimization for the hotplate(s) that display high fluctuations in the hotplate temperature profile and low density CD optimization for the hotplate(s) that display low fluctuations in hotplate temperature profile. Accordingly, wafers that are heat-treated on the hotplate(s) that display higher fluctuations in hotplate temperature profile are inspected at more test areas than wafers that are heat-treated on the hotplate(s) that display lower fluctuations in hotplate temperature.

Thus, for a coating/developing processing system that uses a plurality of hotplates, the method includes establishing temperature profiles for a plurality of hotplate surfaces, wherein each hotplate is divided into a plurality of temperature control zones. The resist coated wafers are heat-treated on the plurality of hotplates. CD metrology data is obtained from test areas on the heat treated wafers, where different groups of test areas are selected for two or more wafers heat-treated on the same hotplate. CD metrology data maps are constructed for each hotplate from the CD metrology data, and adjusted temperature profiles are established for the plurality of hotplate surfaces using the CD metrology data maps.

Thus, for a plurality of hotplates, the number of test areas inspected on the heat-treated wafers may vary, depending on which hotplate was used to heat-treat the wafers. According to one embodiment, the desired wafer throughput may be achieved by varying the number of test areas inspected on the heat-treated wafers. According to another embodiment, wafer throughput may be reduced in order to obtain higher CD metrology data density that provides better CD control and optimization for the hotplate(s) that display high fluctuations in hotplate temperature profile. In other words, higher CD metrology data density may be traded for better CD control and optimization.

Figure 12:
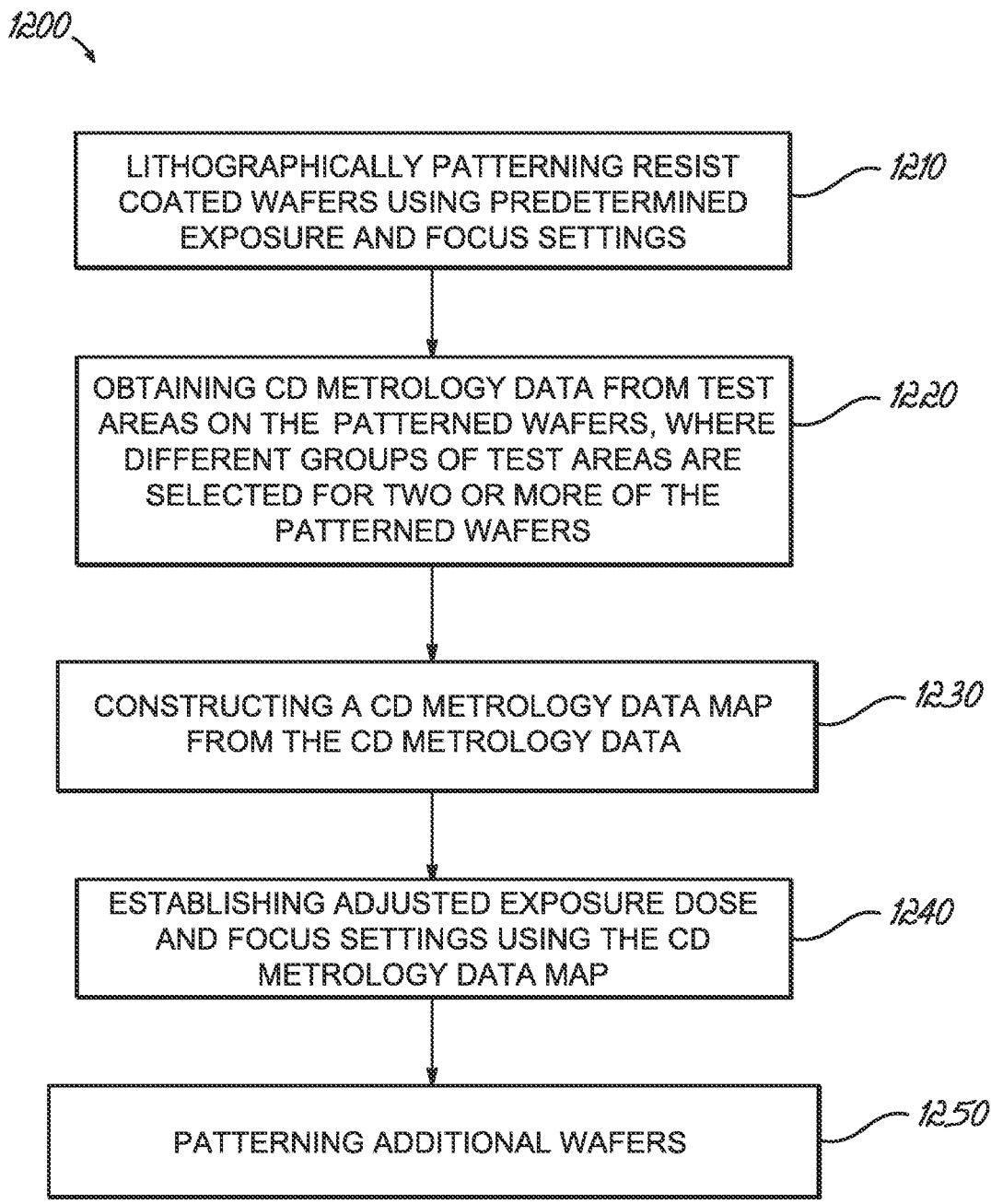
FIG. 12 is a simplified process flow diagram of a method for dynamic CD control and optimization in accordance with another embodiment of the invention.

FIG. 12 is a simplified process flow diagram of a method for dynamic CD control and optimization in accordance with an embodiment of the invention. The process flow 1200 includes, in 1210, lithographically patterning resist coated wafers using predetermined exposure dose and focus settings. The predetermined exposure and focus settings may be based on historical data for the type of wafer and resist.

In 1220, CD metrology data is obtained from test areas on the patterned wafers. According to embodiments of the invention, different groups of test areas are selected for two or more of the patterned wafers. The total number of test areas per wafer may be identical. Alternately, the total number of test areas per wafer may be different. According to one embodiment of the invention, the test areas may form a random pattern on a grid, for example as shown in FIG. 10. According to another embodiment of the invention, the test areas may form a pattern that is rotated a predetermined angle from wafer to wafer. For example, each wafer may be inspected at 5 test areas distributed according to a predetermined pattern over the wafer, where the 5 test area pattern is rotated the predetermined angle from wafer to wafer. In general, the CD metrology data map may have any suitable geometrical arrangement that provides the desired data density across a wafer.

According to one embodiment of the invention, the CD metrology data may be obtained by selecting a desired throughput of processed wafers, and selecting the number of test areas on the processed wafer based on the selected throughput of the processed wafers.

In 1240, a CD metrology data map is constructed from the CD metrology data. The CD metrology map may be constructed by overlaying the CD metrology data at the different test areas. According to one embodiment of the invention, the CD data map may be constructed as a cumulative average or weighted average of CD metrology data from a predetermined number of processed wafers. According to another embodiment of the invention, the CD data map may be constructed as a cumulative average or weighted average of CD metrology data from a predetermined number of consecutively processed wafers.

In 1240, adjusted exposure dose and focus settings are established using the CD metrology data map. The CD metrology data map may be forwarded to a CD optimizer system and the exposure dose and focus settings across a wafer adjusted based on an output of the CD optimizer. The CD optimizer system can utilize an exposure model to improve CD uniformity due to variations in exposure dose and focus across a wafer.

When adjusted exposure dose and focus settings have been established for the lithography tool, additional resist coated wafers may be exposed. According to one embodiment of the invention, the exposure dose and focus may be adjusted between each wafer to be exposed. Alternately, the exposure dose and focus may be adjusted between a predetermined number of wafers to be exposed in 1250.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative system and methods, and illustrative examples shown and described. Accordingly, departures may be made from such details without departing from the scope of applicants' general inventive concept.

What is claimed is:

1. A method of patterning resist coated wafers, the method comprising:
   lithographically patterning resist coated wafers using predetermined exposure dose and focus settings;
   obtaining CD metrology data from test areas on the patterned wafers, wherein different groups of test areas are selected for two or more of the patterned wafers, and wherein the obtaining CD metrology data further comprises selecting a number of test areas on each processed wafer using the equation $$m_{map} = mN - y,$$

wherein $m_{map}$ is the number of different test areas on the patterned wafers, m is the total number of test areas on each patterned wafer, N is the number of patterned wafers, and y is the total number of repeated test areas having the same position on the patterned wafers;
   constructing a CD metrology data map from the CD metrology data; and
   establishing adjusted exposure and/or focus settings using the CD metrology data map.

2. A method of patterning resist coated wafers, the method comprising:
   lithographically patterning resist coated wafers using predetermined exposure dose and focus settings;
   obtaining CD metrology data from test areas on the patterned wafers, wherein different groups of test areas are selected for two or more of the patterned wafers, and wherein the different groups of test areas have an equal number of test areas but a different position for one or more of the test areas;
   constructing a CD metrology data map from the CD metrology data; and
   establishing adjusted exposure and/or focus settings using the CD metrology data map.

3. The method of claim 2, wherein the lithographically patterning comprises:
   exposing the resist coated wafers to light or charged particles;
   sequentially heat-treating the patterned wafers in a post exposure bake (PEB); and
   developing the heat-treated wafers, and
   wherein the method further comprises:
   sequentially heat-treating the developed wafers in a post development bake (PDB).

4. The method of claim 2, wherein the obtaining CD metrology data further comprises:
   selecting a throughput of the patterned wafers; and
   selecting a total number of test areas on each patterned wafer based on the selected throughput of the patterned wafers.

5. The method of claim 2, wherein the CD metrology data is obtained using ODP techniques.

6. The method of claim 2, wherein the establishing adjusted exposure dose and focus settings comprises:
   forwarding the CD metrology map to a CD optimizer system; and
   adjusting the exposure dose, focus, or both, based on an output of the CD optimizer system.

7. The method of claim 2, further comprising:
   patterning additional resist coated wafers after establishing the adjusted exposure dose and/or focus settings.

8. A method of patterning resist coated wafers, the method comprising:
   lithographically patterning resist coated wafers using predetermined exposure dose and focus settings;
   obtaining CD metrology data from test areas on the patterned wafers, wherein different groups of test areas are selected for two or more of the patterned wafers, and wherein the different groups of test areas have a different number of test areas, or a different position for one or more of the test areas, or both;
   constructing a CD metrology data map from the CD metrology data; and
   establishing adjusted exposure and/or focus settings using the CD metrology data map.

9. The method of claim 8, wherein the lithographically patterning comprises:
   exposing the resist coated wafers to light or charged particles;
   sequentially heat-treating the patterned wafers in a post exposure bake (PEB); and
   developing the heat-treated wafers, and
   wherein the method further comprises:
   sequentially heat-treating the developed wafers in a post development bake (PDB).

10. The method of claim 8, wherein the obtaining CD metrology data further comprises:
selecting a throughput of the patterned wafers; and
selecting a total number of test areas on each patterned wafer based on the selected throughput of the patterned wafers.

11. The method of claim 8, wherein the CD metrology data is obtained using ODP techniques.

12. The method of claim 8, wherein the establishing adjusted exposure dose and focus settings comprises:
forwarding the CD metrology map to a CD optimizer system; and
adjusting the exposure dose, focus, or both, based on an output of the CD optimizer system.

13. The method of claim 8, further comprising:
patterning additional resist coated wafers after establishing the adjusted exposure dose and/or focus settings.

14. A method of patterning resist coated wafers, the method comprising:
lithographically patterning resist coated wafers using predetermined exposure dose and focus settings;
obtaining CD metrology data from test areas on the patterned wafers, wherein different groups of test areas are selected for two or more of the patterned wafers;
constructing a CD metrology data map from the CD metrology data by overlaying the CD metrology data from each test area, wherein the overlaying comprises averaging the CD metrology data at each test area as a cumulative average or a weighted cumulative average of a predetermined number of patterned wafers; and
establishing adjusted exposure and/or focus settings using the CD metrology data map.

15. The method of claim 14, wherein the overlaying comprises:
averaging the CD metrology data at each test area as a cumulative average or a weighted cumulative average of a predetermined number of consecutively patterned wafers.

16. A method of patterning resist coated wafers, the method comprising:
lithographically patterning resist coated wafers using predetermined exposure dose and focus settings, wherein the patterning comprises exposing the resist coated wafers to light or charged particles, sequentially heat-treating the patterned wafers in a post exposure bake (PEB), and developing the heat-treated wafers;
obtaining CD metrology data from test areas on the patterned wafers using ODP techniques, wherein different groups of test areas are selected for two or more of the patterned wafers and the different groups of test areas have equal number of test areas but a different position for one or more of the test areas;
constructing a CD metrology data map from the CD metrology data by overlaying the CD metrology data from each test area;
establishing adjusted exposure and/or focus settings using the CD metrology data map by forwarding the CD metrology map to a CD optimizer system and adjusting the exposure dose, focus, or both, based on an output of the CD optimizer system; and
patterning additional resist coated wafers after establishing the adjusted exposure dose and/or focus settings.

17. The method of claim 16, wherein the overlaying comprises:
averaging the CD metrology data at each test area as a cumulative average or a weighted cumulative average of a predetermined number of patterned wafers.

18. The method of claim 16, wherein the overlaying comprises:
averaging the CD metrology data at each test area as a cumulative average or a weighted cumulative average of a predetermined number of consecutively patterned wafers.

19. A method of patterning resist coated wafers, the method comprising:
lithographically patterning resist coated wafers using predetermined exposure dose and focus settings, wherein the patterning comprises exposing the resist coated wafers to light or charged particles, sequentially heat-treating the patterned wafers in a post exposure bake (PEB), and developing the heat-treated wafers;
obtaining CD metrology data from test areas on the patterned wafers using ODP techniques, wherein different groups of test areas are selected for two or more of the patterned wafers and the different groups of test areas have a different number of test areas, or a different position for one or more of the test areas, or both;
constructing a CD metrology data map from the CD metrology data by overlaying the CD metrology data from each test area;
establishing adjusted exposure and/or focus settings using the CD metrology data map by forwarding the CD metrology data map to a CD optimizer system and adjusting the exposure dose, or focus, or both, based on an output of the CD optimizer system; and
patterning additional resist coated wafers after establishing the adjusted exposure dose and/or focus settings.

20. The method of claim 19, wherein the overlaying comprises:
averaging the CD metrology data at each test area as a cumulative average or a weighted cumulative average of a predetermined number of patterned wafers.

21. The method of claim 19, wherein the overlaying comprises:
averaging the CD metrology data at each test area as a cumulative average or a weighted cumulative average of a predetermined number of consecutively patterned wafers.

* * * * *

UNITED STATES PATENT AND TRADEMARK OFFICE
CERTIFICATE OF CORRECTION

PATENT NO. : 7,483,804 B2  Page 1 of 1
APPLICATION NO. : 11/537085
DATED : January 27, 2009
INVENTOR(S) : Steven Scheer It is certified that error appears in the above-identified patent and that said Letters Patent is hereby corrected as shown below:

Col. 1, line 14, "HEAT-TREANING" should read --HEAT-TREATING--.

Col. 14, line 5, "predetermines number" should read --predetermined number--.

Signed and Sealed this

Twenty-seventh Day of October, 2009

David J. Kappos
*Director of the United States Patent and Trademark Office*